(12) United States Patent
Kiesele et al.

(10) Patent No.: US 6,793,786 B2
(45) Date of Patent: Sep. 21, 2004

(54) FLOW GAP GAS DISTRIBUTION ADAPTER FOR AN ELECTROCHEMICAL GAS SENSOR

(75) Inventors: Herbert Kiesele, Lübeck (DE); Uwe Kühn, Wesenberg (DE); Rainer Kunz, Lübeck (DE); Frank Mett, Lübeck (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 40 days.

(21) Appl. No.: 10/109,477

(22) Filed: Mar. 28, 2002

(65) Prior Publication Data

US 2003/0010635 A1 Jan. 16, 2003

(30) Foreign Application Priority Data

Jul. 13, 2001 (DE) .......................................... 101 34 140

(51) Int. Cl.[7] ..................... G01N 27/404; G01N 27/416
(52) U.S. Cl. ...................................... 204/409; 204/415
(58) Field of Search ............................... 204/409, 415; 205/782, 782.5, 783

(56) References Cited

U.S. PATENT DOCUMENTS

| 3,622,487 | A | * | 11/1971 | Chand et al. |
| 3,957,611 | A | * | 5/1976 | Moll et al. |
| 3,988,233 | A | * | 10/1976 | Gamer et al. |
| 4,017,373 | A |   | 4/1977 | Shaw et al. |
| 4,092,233 | A | * | 5/1978 | Clemens et al. |
| 4,152,233 | A | * | 5/1979 | Chand |
| 4,172,770 | A | * | 10/1979 | Semersky et al. |
| 4,522,699 | A | * | 6/1985 | Novak et al. |
| 4,533,456 | A | * | 8/1985 | Kratchvil et al. |
| 4,950,379 | A | * | 8/1990 | Young et al. |
| 5,690,808 | A |   | 11/1997 | Akmal et al. |
| 5,700,360 | A | * | 12/1997 | Chan et al. |
| 5,759,368 | A | * | 6/1998 | Kuhn |

FOREIGN PATENT DOCUMENTS

| DE | 196 19 169 C2 | 11/1997 |
| DE | 197 10 527 A1 | 9/1998 |

* cited by examiner

*Primary Examiner*—Kaj K. Olsen
(74) *Attorney, Agent, or Firm*—McGlew and Tuttle, P.C.

(57) ABSTRACT

An adapter (1) and electrochemical gas sensor (2) is provided with an electrochemical gas sensor housing (14) accommodating an electrolyte (13), with at least one measuring electrode (12) arranged therein and with a membrane (11), which screens the measuring electrode (12) from a measured gas and is permeable to the measured gas. The measuring sensitivity of an electrochemical gas sensor is increased by the adapter (1) having a gas-impermeable surface (15) extending in parallel to and at a spaced location from the membrane (11). The adapter (1) and the membrane (11) form a flow gap (10) for the measured gas delivered by a pump. The adapter (1) may be plugged onto the electrochemical sensor (2) at its outer edge (1a). The measured gas enters through a central opening (17), expands in the flow gap (10) radially to the outside and leaves same via the ring-shaped gap (16).

15 Claims, 5 Drawing Sheets

FLOW GAP GAS DISTRIBUTION ADAPTER FOR AN ELECTROCHEMICAL GAS SENSOR

FIELD OF THE INVENTION

The present invention pertains to an adapter for an electrochemical gas sensor with a housing accommodating an electrolyte, at least one measuring electrode arranged therein, and a membrane that screens the measuring electrode from a measured gas and is permeable to the measured gas.

BACKGROUND OF THE INVENTION

In an electrochemical gas sensor, the measured gas diffuses through a membrane into the electrolyte of the sensor. A measuring electrode, at which the measured gas is electrochemically converted, is located in the electrolyte. A current, which generates a measured signal, flows through the electrochemical gas sensor. The value of the measured signal is determined by the rate of the signal-generating process taking place at the electrode. It depends on the so-called mass transport (diffusion and optionally convection), on the one hand, and, on the other hand, on the resulting overall rate of the reaction taking place at the electrode, which may consist in turn of a plurality of partial steps (adsorption/desorption, homogeneous reactions, heterogeneous reactions, charge transfer, phase formation).

Electrochemical gas sensors are designed, in general, such that the mass transport is the rate-determining partial step, because a linear concentration dependence of the signal can thus be achieved and the sensor has a substantially higher long-term stability.

In a transport-controlled process taking place at the electrode, the resulting sensor current depends on the concentration gradient or the layer thickness of the depletion zone in front of the measuring electrode. If the sensor is operated in the diffusion mode, a spherical depletion zone is formed, which greatly limits the signal amplitude and may also be interfered with by ventilation.

If gas is actively admitted to the sensor, more or less linear gradients are formed depending on the geometry and the velocity of flow.

U.S. Pat. No. 4,017,373 shows an electrochemical gas sensor with a flow gap for the measured gas, wherein the feed and removal of the measured gas to and from the measuring electrode take place via thin pipelines.

DE 196 19 169 C2 describes an electrochemical gas sensor with at least two electrodes, with an electrode carrier and with an electrolyte in a housing made of a material that is impermeable to electrolyte. The otherwise closed housing has an inlet capillary and an outlet capillary for the measured gas, so that an interaction is ensured between the measured gas sample and the measuring electrode in the electrochemical gas sensor, but the diffusion of moisture from the environment into the interior of the housing is prevented from occurring at the same time. The drawback of the prior-art electrochemical gas sensor is that the measuring sensitivity is low, so that low gas concentrations to be measured cannot be determined.

SUMMARY AND OBJECTS OF THE INVENTION

The object of the present invention is to increase the measuring sensitivity of an electrochemical gas sensor.

According to the invention, an adapter is provided intended for an electrochemical gas sensor with a housing accommodating an electrolyte. At least one measuring electrode and a membrane are arranged in the housing. The membrane screens the measuring electrode from a measured gas and is permeable to the measured gas. The measured gas will be defined below as both a measured gas in a gas mixture and a measured gas dissolved in a liquid. An inlet for feeding the measured gas to the side of the membrane located opposite the measuring electrode is formed either by the adapter or by the housing or by the adapter and the housing together. If the inlet for feeding in the measured gas is formed by the adapter and the housing together, the two parts have a geometry that releases the inlet for the measured gas when the parts are fitted together.

An outlet for removing the measured gas from the side of the membrane located opposite the measuring electrode is correspondingly formed by the adapter or by the housing or by the adapter and the housing together.

Between the inlet and the outlet, the adapter has a gas-impermeable surface extending in parallel to and at a spaced location from the membrane, so that the adapter and the membrane form a flow gap for the measured gas, a so-called capillary gap. A corresponding adapter is also called a capillary gap gas distribution adapter. The adapter can be connected to a pump, so that the measured gas fed in is sent through the gap by means of the pressure generated by the pump when the pump is arranged upstream or by the suction when the pump is arranged downstream. Due to the fact that the measured gas is passed through a flow gap, which is limited by two surfaces, namely, the gas-impermeable surface of the adapter and the membrane, good diffusion of the measured gas through the membrane and thus a measuring sensitivity of the electrochemical gas sensor that is improved many times is guaranteed.

In a first embodiment, the flow gap has an essentially parallelepipedic shape, with two lateral limiting walls extending vertically between the flat membrane and the gas-impermeable surface.

In a second embodiment, the flow gap is of a radially symmetrical design. The membrane and the gas-impermeable surface have the shape of circular disks. A central opening in the gas-impermeable surface acts either as an inlet for feeding in the measured gas or as an outlet for removing the measured gas. A ring-shaped gap is provided between the edge of the gas-impermeable surface shaped as a circular disk with a central opening and the housing. The measured gas is fed in via the central opening in the gas-impermeable surface, after which it is passed radially to the outside through the flow gap and is removed via the ring-shaped gap.

This is especially advantageous because the velocity of flow decreases in the radial direction because of the continuity equation. As a result, the residence time of the measured gas at the membrane increases with increasing depletion due to the reaction with the electrolyte, so that little time is available for the diffusion of the gas through the membrane in areas with high measured gas concentration, and much time is available for this diffusion in areas with low concentration.

However, it is conversely also conceivable that the measured gas is fed in via the ring-shaped gap. It is then passed through the flow gap radially in the inward direction and is removed via the central opening in the gas-impermeable surface.

A third embodiment provides for a rotationally symmetrical design of the flow gap with the membrane formed as an outer cylinder jacket around the axis of rotation and with the gas-impermeable surface, which is formed as an inner cylinder jacket and is arranged coaxially to the outer cylinder jacket. An alternative variant of the third embodiment provides for the membrane being designed as an inner cylinder jacket and the gas-impermeable surface as an outer cylinder jacket. The measured gas is passed through the flow gap in parallel to the axis of rotation in both cases.

In a special design of the third embodiment and its alternative variant, the outer cylinder jacket is limited by a gas-impermeable outer cylinder bottom extending at right angles to the axis of rotation. The inner cylinder jacket is limited by an inner cylinder bottom, which is located at a spaced location from the outer cylinder bottom. A central hole, through which measured gas is either fed in or is passed to the outside to the flow gap or is, conversely, removed, after it was passed radially in the inward direction from the flow gap, is located in the inner cylinder bottom.

An additional embodiment is represented by an adapter detachably connected to the housing of the electrochemical gas sensor. A plug-type connection may be provided which optionally snaps in, or has a screw connection.

As an alternative to this, the adapter is firmly connected to the housing of the electrochemical gas sensor, especially in one piece as part of the housing of the electrochemical gas sensor.

In a preferred embodiment, the flow gap has a gap width of at most 2.5 mm. Optimal mass transport of the measured gas being sent by the membrane due to diffusion is guaranteed in this size range.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
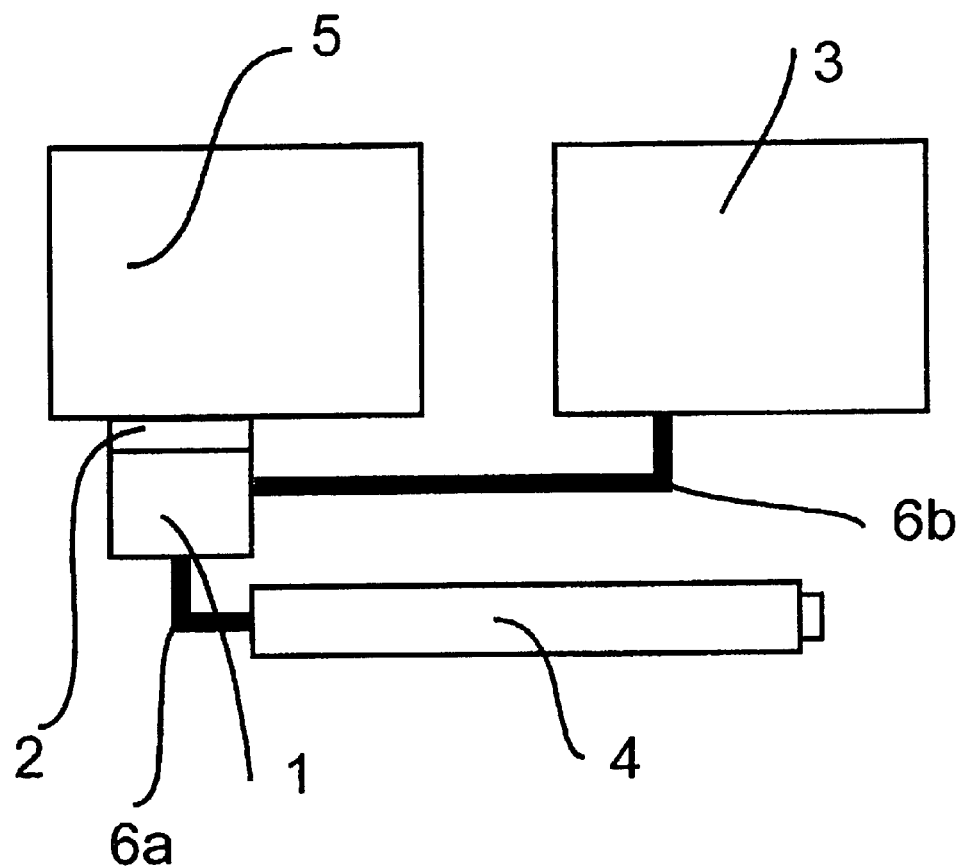
FIG. 1 is a schematic view of an arrangement for measuring gases, with an adapter, an electrochemical gas sensor, a pump, and a conditioning unit, as well as an evaluating unit.

Referring to the drawings in particular, FIG. 1 schematically shows an arrangement for measuring gases. The arrangement comprises an electrochemical gas sensor 2 and an adapter 1 connected to same. A measured gas enters the adapter 1 from a conditioning means 4 via a feed tube 6a. The measured gas (i.e., the gas to be measured) is then sent into a flow gap, which is not shown in FIG. 1. The gas measurement takes place in a unit formed by the adapter 1 and the electrochemical gas sensor 2, from which the received signals resulting from the gas measurement are passed on to an evaluating unit 5. The measured gas is drawn off from the flow gap via the adapter 1 through a discharge tube 6b. The removal is ensured by a pump 3 connected to the discharge tube 6b.

The conditioning means 4 can condition the measured gas before it is fed into the adapter 1 in a simple manner. Undesired moisture can be removed from the measured gas by sending it, e.g., into the conditioning means 4 through a NAFION® tube, not shown. The moisture present in the measured gas can also be adapted to the water vapor pressure of the electrolyte. The desired temperature of the measured gas can be obtained by means of heating or cooling elements in the conditioning means 4, which are not shown in FIG. 1. In addition, it is possible to remove gaseous components, to release the analyte from an aqueous solution or to chemically modify it. This shall be illustrated by the following examples:

Hydrogen peroxide or ozone in the measured gas can be removed by means of a platinum catalyst in the conditioning means 4, which is likewise not shown.

Ammonia dissolved in water can be released as a gas by adding an alkali.

For example, chlorinated hydrocarbons can be decomposed by pyrolysis at a hot wire and the resulting gases (chlorine and hydrogen chloride) can be sensitively detected at the sensor.

The conditioning means 4 is arranged upstream of the arrangement comprising the gas sensor 2 and the adapter 1 either separately, as is shown in FIG. 1, or it is integrated within the arrangement.

Figure 2:
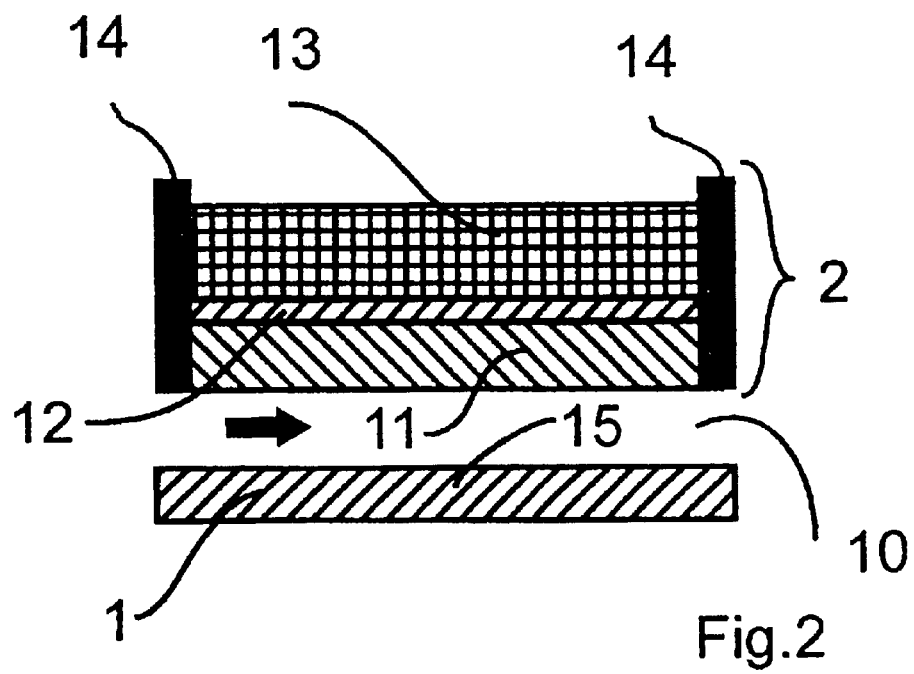
FIG. 2 is a longitudinal sectional view of an adapter and an electrochemical gas sensor in parallel to the direction of flow with an essentially parallelepipedic flow gap.

FIG. 2 schematically shows the longitudinal section of an adapter 1 and an electrochemical gas sensor 2 in parallel to the direction of flow, wherein the measured gas flows through the flow gap 10 in the direction of the arrow. The flow gap 10 is limited from below by a gas-impermeable surface 15 of the adapter 1 and is screened from the top by a membrane 11 of the electrochemical gas sensor 2, which extends in parallel to and at a spaced location from the surface and screens the measuring electrode 12 from the measuring gas. An electrolyte 13 is located on the side of the membrane 11 located opposite the measured gas next to the measuring electrode 12. The membrane 11, the measuring electrode 12 and the electrolyte 13 are accommodated by an electrolyte-impermeable housing 14 of the electrochemical gas sensor 2.

Figure 3:
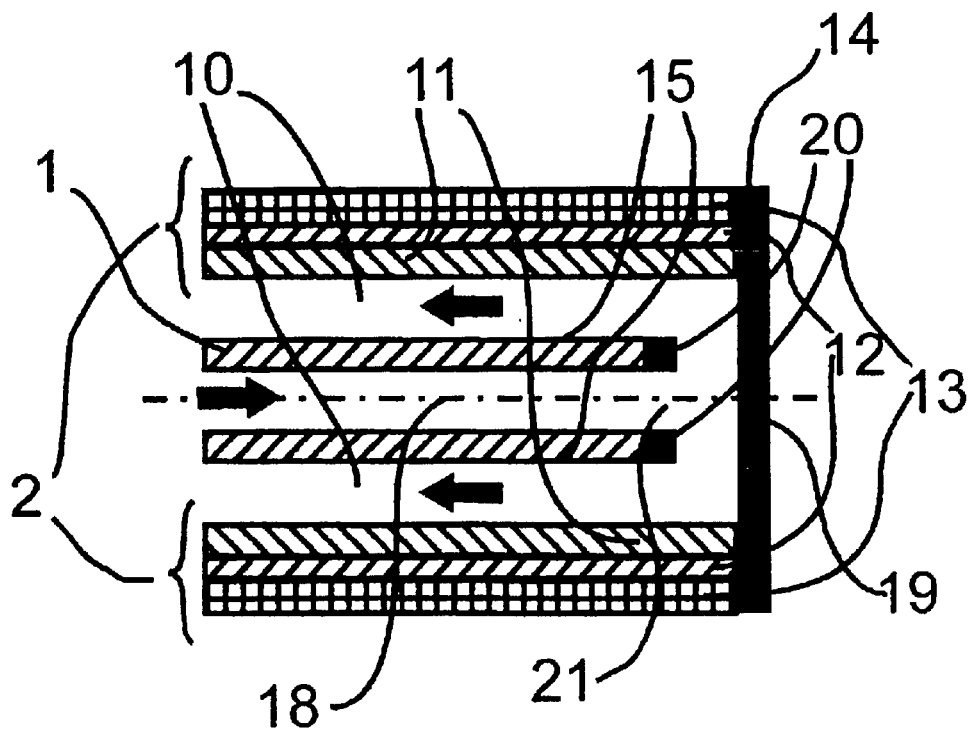
FIG. 3 is a longitudinal sectional view of an adapter and an electrochemical gas sensor with a rotationally symmetrical flow gap through the axis of rotation with a membrane formed as an outer cylinder jacket around the axis of rotation and with a gas-impermeable surface formed as an inner cylinder jacket, wherein cylinder bottoms extend at right angles to the axis of rotation and are arranged at a spaced location limit the respective outer and inner cylinder jackets.

FIG. 3 shows the longitudinal section of an adapter 1 and an electrochemical gas sensor 2 with a rotationally symmetrical flow gap 10 through the axis of rotation 18 with a membrane 11 formed as an outer cylinder jacket around the axis of rotation and with a gas-impermeable surface 15, which is shaped coaxially thereto as an inner cylinder jacket. An outer cylinder bottom 19, which limits the outer cylinder jacket, and an inner cylinder bottom 20, which limits the inner cylinder jacket, extend at right angles to the axis of rotation 18. The two cylinder jackets 19 and 20 are arranged in parallel to and at spaced locations from one another. The measured gas flows in through a channel that extends along the axis of rotation 18 and is surrounded by the inner cylinder jacket, it expands from a central hole 21 in the inner cylinder bottom 20 radially to the outside and subsequently flows in the opposite direction through the flow gap 10 formed in a ring-shaped pattern between the two cylinder surfaces. The membrane 11 formed as an outer cylinder jacket is surrounded toward the outside by the measuring electrode 12 and the electrolyte 13, which are thus screened from the measured gas flowing into the flow gap 10. The membrane 11, the measuring electrode 12, and the electrolyte 13 are surrounded by the housing 14, which is partially shown in FIG. 3. Flow of the measured gas through the flow gap 10 in the opposite direction, which is not shown in FIG. 3, is also possible, in principle. After flowing through the flow gap 10, the measured gas now flows radially inwardly and is subsequently removed via the central hole 21 in the inner cylinder jacket.

If the radius of the membrane 11 is, e.g., 6 mm, the width of the flow gap 10 is 1 mm and the volume flow rate of the measured gas is 500 mL per minute, the velocity of flow of the measured gas at the outer circumference of the membrane 11 is approximately 221 mm per sec, and the air exchange rate is approximately 73.1 times per sec. The $t_{0/90}$ time, which is the indicator for the response time of the electrochemical gas sensor 2, is found to be 30 msec from this for the linear transverse diffusion according to Fick's first law. This means that the measured gas had already left the flow gap 10 before the diffusion-determined concentration gradient developed completely. As a result, the measuring sensitivity of the electrochemical gas sensor 2 is markedly increased.

Figure 4:
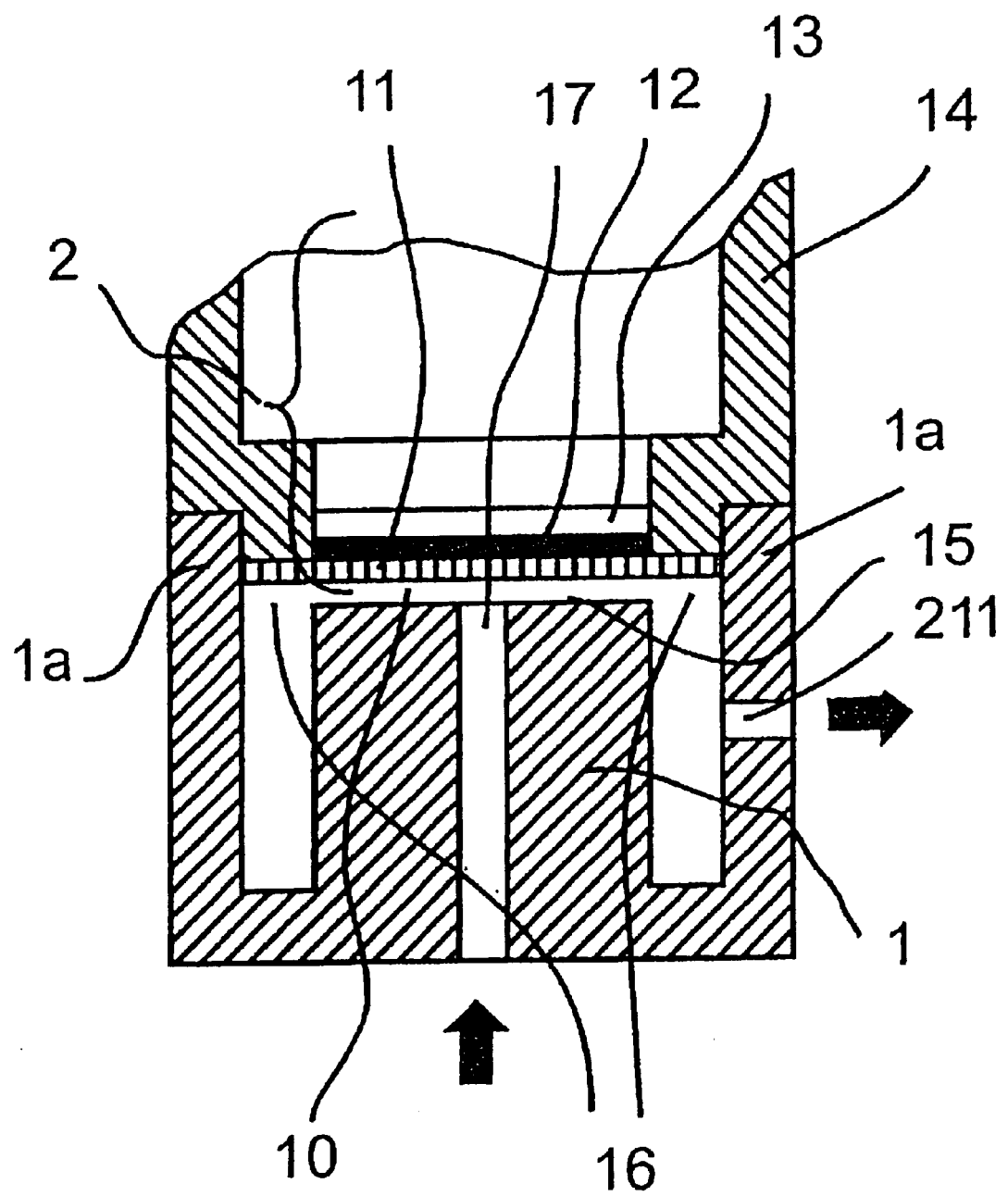
FIG. 4 is a longitudinal sectional view of an adapter and an electrochemical gas sensor with radially symmetrical flow gap.

FIG. 4 shows the longitudinal section of an adapter 1 and an electrochemical gas sensor 2 in the direction of flow. The adapter 1 and the electrochemical gas sensor 2 are connected to one another via a plug-type connection, with the adapter 1 surrounding the electrochemical gas sensor 2 at its outer edge 1*a* in a ring-shaped pattern. The membrane 11 and the gas-impermeable surface 15 are shaped as circular disks, the gas-impermeable surface 15 having a central opening 17, through which the measured gas enters the flow gap 10 formed by the membrane 11 and the gas-impermeable surface 15 in the direction of the arrow, it flows radially to the outside there and reaches a ring-shaped gap 16. The measured gas leaves the adapter 1 in the direction of the arrow via a discharge opening 211 arranged laterally in the ring-shaped gap 16 of the adapter 1. The membrane 11 is arranged in a housing 14 of the electrochemical gas sensor 2 and it screens the measuring electrode 12, which is likewise arranged in the housing 14, and the electrolyte 13 from the measured gas. It is also conceivable, albeit not shown here, that the measured gas flows through the arrangement according to FIG. 4 in the opposite direction.

Figure 5:
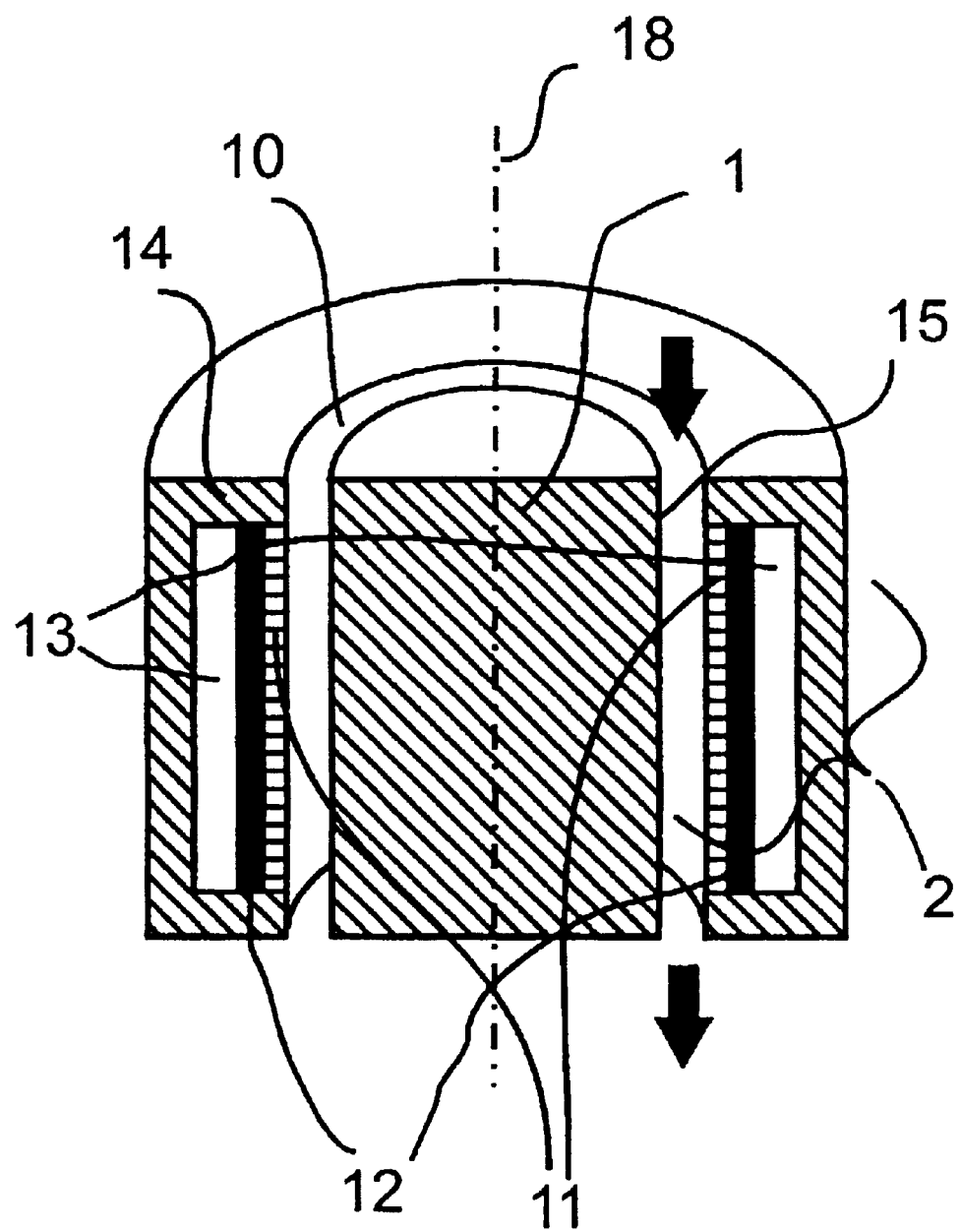
FIG. 5 is a longitudinal sectional view of an adapter and an electrochemical gas sensor with a rotationally symmetrical flow gap through the axis of rotation with a membrane formed as an outer cylinder jacket around the axis of rotation and with a gas-impermeable surface formed as an inner cylinder jacket.
Figure 6:
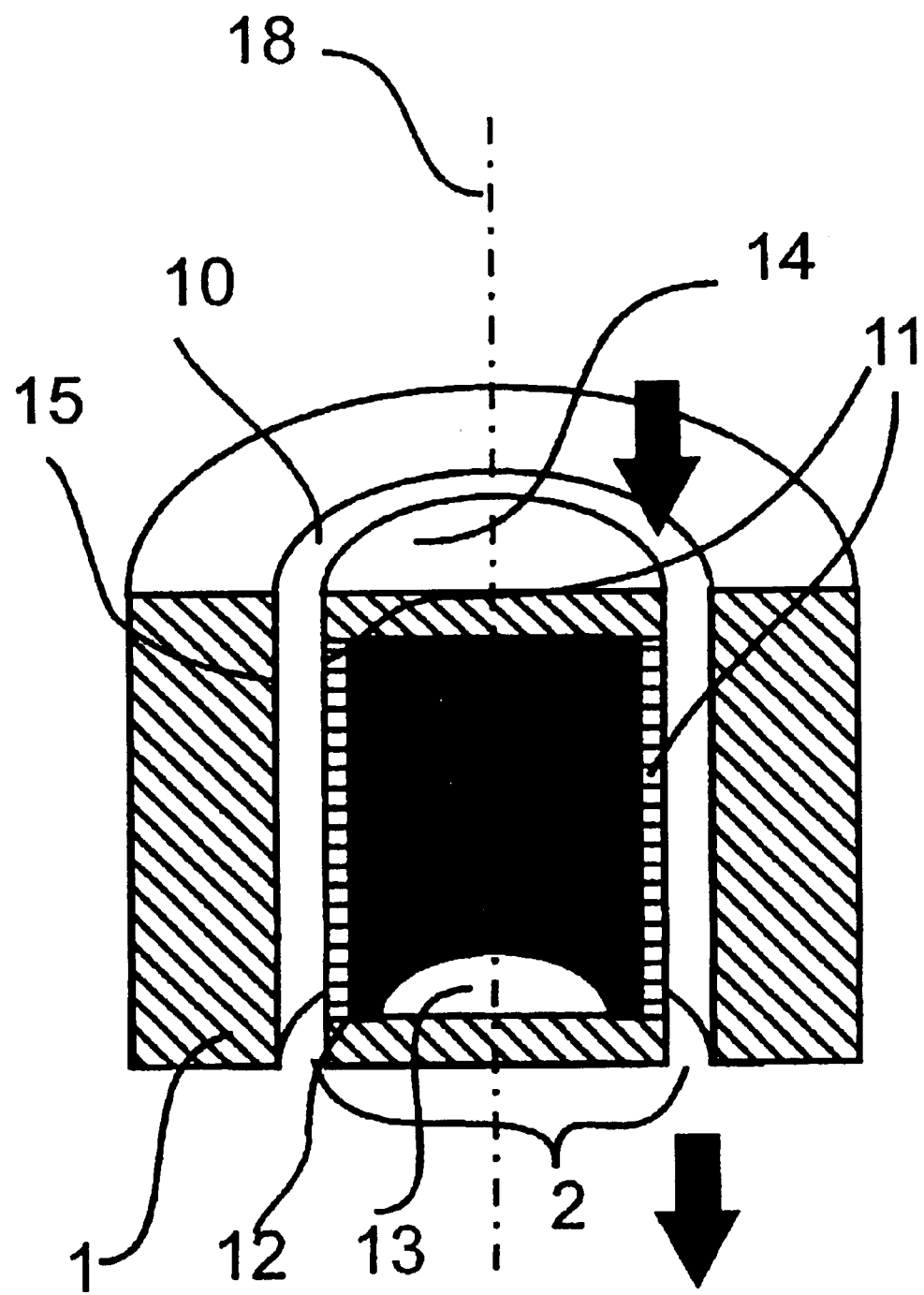
FIG. 6 is a longitudinal sectional view of an adapter and an electrochemical gas sensor with a rotationally symmetrical flow gap through the axis of rotation with a gas-impermeable surface formed as an outer cylinder jacket around the axis of rotation and with a membrane formed as an inner cylinder jacket.

FIGS. 5 and 6 show the longitudinal section of an adapter 1 and an electrochemical gas sensor 2 each with rotationally symmetrical flow gap 10 through the axis of rotation 18, which is limited by an outer cylinder jacket and an inner cylinder jacket. The two arrangements in FIG. 5 and FIG. 6 differ in that the outer cylinder jacket is formed by the membrane 11 and the inner cylinder jacket is formed by the gas-impermeable surface 15 in FIG. 5, whereas, conversely, the outer cylinder jacket is formed by the gas-impermeable surface 15 and the inner cylinder jacket is formed by the membrane 11 in FIG. 6. In both embodiments, the membrane 11 screens the measuring electrode 12 and the electrolyte 13 from the measured gas flowing on the opposite side of the membrane 11, which measured gas flows in the flow gap 10 formed as a ring-shaped channel. The membrane 11, the measuring electrode 12 and the electrolyte 13 are surrounded by the housing 14 of the electrochemical gas sensor 2. The measured gas flows through the flow gap 10, represented as arrows pointing vertically downward, in parallel to the axis of rotation 18 in both arrangements.

While specific embodiments of the invention have been shown and described in detail to illustrate the application of the principles of the invention, it will be understood that the invention may be embodied otherwise without departing from such principles.

What is claimed is:

1. An adapter and an electrochemical gas sensor, comprising:

an electrochemical gas sensor housing accommodating an electrolyte;

a measuring electrode arranged in the housing in contact with the electrolyte;

a membrane that screens the measuring electrode and the electrolyte from the measured gas and is permeable to the measured gas for mass exchange between the electrolyte and the measured gas;

an adapter with a gas-impermeable surface, the adapter and the electrochemical gas sensor housing forming an inlet for feeding in a measured gas to the side of the membrane located opposite the measuring electrode, the adapter and the housing forming an outlet for removing the measured gas from the side of the membrane located opposite the measuring electrode, the adapter gas-impermeable surface extending in parallel to and at a spaced location from the membrane between the inlet and the outlet for the measured gas, the adapter and the membrane cooperating to form a flow gap for the measured gas, wherein the flow gap has a rotationally symmetrical design with the membrane shaped as an outer cylinder jacket formed around an axis of rotation and with the gas-impermeable surface shaped as an inner cylinder jacket and arranged coaxially with the outer cylinder jacket.

2. An adapter and an electrochemical gas sensor in accordance with claim 1, wherein a gas-impermeable outer cylinder bottom extending at right angles to the axis of rotation limits the outer cylinder jacket and an inner cylinder bottom which is extending at right angles to the axis of rotation and has a central hole and limits the inner cylinder jacket as an inlet or outlet for the measured gas, wherein the inner cylinder bottom and the outer cylinder bottom are arranged at spaced locations from one another.

3. An adapter and an electrochemical gas sensor, comprising:

an electrochemical gas sensor housing accommodating an electrolyte;

a measuring electrode arranged in the housing in contact with the electrolyte;

a membrane that screens the measuring electrode and the electrolyte from the measured gas and is permeable to the measured gas for mass exchange between the electrolyte and the measured gas;

an adapter with a gas-impermeable surface, the adapter and the electrochemical gas sensor housing forming an inlet for feeding in a measured gas to the side of the membrane located opposite the measuring electrode, the adapter and the housing forming an outlet for removing the measured gas from the side of the membrane located opposite the measuring electrode, the adapter gas-impermeable surface extending in parallel to and at a spaced location from the membrane between the inlet and the outlet for the measured gas, the adapter and the membrane cooperating to form a flow gap for the measured gas, wherein the flow gap has a rotationally symmetrical design with the gas-impermeable surface formed as an outer cylinder jacket around the axis of rotation and with the membrane formed as an inner cylinder jacket and arranged coaxially with the outer cylinder jacket.

4. An adapter and an electrochemical gas sensor in accordance with claim 3, wherein a gas-impermeable outer cylinder bottom extending at right angles to the axis of rotation limits the outer cylinder jacket and an inner cylinder bottom extending at right angles to the axis of rotation and limiting the inner cylinder jacket, wherein the inner cylinder bottom and the outer cylinder bottom are arranged at spaced locations from one another.

5. An adapter and an electrochemical gas sensor in accordance with claim 3, wherein the adapter is detachably connected to the housing of the electrochemical gas sensor by a plug connection.

6. An adapter and an electrochemical gas sensor in accordance with claim 3, wherein the adapter is firmly connected to the electrochemical gas sensor housing and is manufactured in one piece as part of the electrochemical gas sensor housing.

7. An adapter and an electrochemical gas sensor in accordance with claim 3, wherein the flow gap has a gap width of at most 2.5 mm.

8. An adapter and electrochemical gas sensor combination, comprising:
    an electrochemical gas sensor housing accommodating an electrolyte;
    a measuring electrode arranged in said housing;
    a membrane that screens the measuring electrode and electrolyte from the measured gas and is permeable to the measured gas; and
    an adapter, the adapter and the electrochemical gas sensor housing forming an inlet for feeding in a measured gas to a side of the membrane located opposite the measuring electrode and electrolyte, the adapter and the housing forming an outlet for removing the measured gas from a side of the membrane located opposite the measuring electrode and electrolyte, the adapter having a gas-impermeable surface extending in parallel to and at a spaced location from the membrane between the inlet and the outlet for the measured gas, the adapter and the membrane cooperating to form a flow gap for the measured gas, wherein the flow gap has a radially symmetrical design with the membrane shaped as a circular disk and with the gas-impermeable surface shaped as a circular disk with a central opening as the inlet or outlet for the measured gas.

9. A combination in accordance with claim 8, wherein a ring-shaped gap is provided between the edge of the gas-impermeable surface shaped as a circular disk with a central opening and an adapter housing portion.

10. An adapter and electrochemical gas sensor combination, comprising:
    an electrochemical gas sensor housing accommodating an electrolyte;
    a measuring electrode arranged in said housing;
    a membrane that screens the measuring electrode and electrolyte from the measured gas and is permeable to the measured gas; and
    an adapter, the adapter and the electrochemical gas sensor housing forming an inlet for feeding in a measured gas to a side of the membrane located opposite the measuring electrode and electrolyte, the adapter and the housing forming an outlet for removing the measured gas from a side of the membrane located opposite the measuring electrode and electrolyte, the adapter having a gas-impermeable surface extending in parallel to and at a spaced location from the membrane between the inlet and the outlet for the measured gas, the adapter and the membrane cooperating to form a flow gap for the measured gas, wherein the flow gap has a rotationally symmetrical design with the membrane shaped as an outer cylinder jacket formed around an axis of rotation and with the gas-impermeable surface shaped as an inner cylinder jacket and arranged coaxially with the outer cylinder jacket.

11. A combination in accordance with claim 10, wherein a gas-impermeable outer cylinder bottom extending at right angles to the axis of rotation limits the outer cylinder jacket and a inner cylinder bottom extending at right angles to the axis of rotation has a central hole and limits the inner cylinder jacket as an inlet or outlet for the measured gas, wherein the inner cylinder bottom and the outer cylinder bottom are arranged at spaced locations from one another.

12. An adapter and electrochemical gas sensor combination, comprising:
    an electrochemical gas sensor housing accommodating an electrolyte;
    a measuring electrode arranged in said housing;
    a membrane that screens the measuring electrode and electrolyte from the measured gas and is permeable to the measured gas; and
    an adapter, the adapter and the electrochemical gas sensor housing forming an inlet for feeding in a measured gas to a side of the membrane located opposite the measuring electrode and electrolyte, the adapter and the housing forming an outlet for removing the measured gas from a side of the membrane located opposite the measuring electrode and electrolyte, the adapter having a gas-impermeable surface extending in parallel to and at a spaced location from the membrane between the inlet and the outlet for the measured gas, the adapter and the membrane cooperating to form a flow gap for the measured gas, wherein the flow gap has a rotationally symmetrical design with the gas-impermeable surface formed as an outer cylinder jacket around the axis of rotation and with the membrane formed as an inner cylinder jacket and arranged coaxially with the outer cylinder jacket.

13. A combination in accordance with claim 12, wherein a gas-impermeable outer cylinder bottom extending at right angles to the axis of rotation limits the outer cylinder jacket and a inner cylinder bottom extending at right angles to the axis of rotation and limiting the inner cylinder jacket, wherein the inner cylinder bottom and the outer cylinder bottom are arranged at spaced locations from one another.

14. A combination in accordance with claim 12, wherein the flow gap has a gap width of at most 2.5 mm.

15. An electrochemical gas sensing system comprising:

an electrochemical gas sensor housing defining an electrolyte space;

electrolyte disposed in said electrolyte space;

a measuring electrode arranged in said electrolyte space;

a membrane closing off said electrolyte space and defining a gas permeable liquid impermeable barrier screening said electrolyte and said measuring electrode with respect to a gas space outside of said electrolyte space;

an adapter, said adapter and the electrochemical gas sensor housing forming an inlet for feeding in a measured gas to the gas space at a side of the membrane located opposite said electrolyte space, the adapter and the housing forming an outlet for removing the measured gas the gas space opposite said electrolyte space, the adapter having a gas-impermeable surface extending in parallel to and at a spaced location from the membrane to form a gas flow gap between the gas inlet and the gas outlet the flow gap having a rotationally symmetrical design with the gas-impermeable surface formed as one of an outer cylinder jacket around the axis of rotation and an inner cylinder jacket arranged coaxially with the outer cylinder jacket and with the membrane formed as the other of the outer cylinder jacket and the inner cylinder jacket; and a pump connected to one of said gas inlet and said gas outlet for causing measured gas to flow through said gas flow gap.

* * * * *